US012702799B2

(12) United States Patent
Kim et al.

(10) Patent No.: US 12,702,799 B2
(45) Date of Patent: Aug. 11, 2026

(54) METHODS AND SYSTEMS FOR AUTOMATED STEERING OF GUIDEWIRES

(71) Applicant: Magnendo Corp., Newton, MA (US)

(72) Inventors: Yoonho Kim, Boston, MA (US); Jaehun Choe, Cambridge, MA (US)

( * ) Notice: Subject to any disclaimer, the term of this patent is extended or adjusted under 35 U.S.C. 154(b) by 0 days.

(21) Appl. No.: 19/346,106

(22) Filed: Sep. 30, 2025

(65) Prior Publication Data

US 2026/0091201 A1 Apr. 2, 2026

Related U.S. Application Data

(60) Provisional application No. 63/701,693, filed on Oct. 1, 2024.

(51) Int. Cl.
*A61M 25/01* (2006.01)
*A61B 34/00* (2016.01)
(Continued)

(52) U.S. Cl.
CPC ......... *A61M 25/0158* (2013.01); *A61B 34/10* (2016.02); *A61B 34/25* (2016.02);
(Continued)

(58) Field of Classification Search
CPC ........ A61M 25/0158; A61M 25/09041; A61B 2034/301; A61B 2034/107; A61B 2034/105
See application file for complete search history.

(56) References Cited

U.S. PATENT DOCUMENTS 6,400,980 B1 * 6/2002 Lemelson ...... A61B 17/320758 600/478
8,394,091 B2 * 3/2013 Rioux ............... A61M 25/0127 606/41
(Continued)

FOREIGN PATENT DOCUMENTS

CN 114025658 A * 2/2022 ........... G06N 3/0455
CN 115253023 A * 11/2022 ............. A61B 34/70
(Continued)

OTHER PUBLICATIONS

International Search Report and Written Opinion issued in App. No. PCT/US2025/048902 dated Jan. 29, 2026 (pp. 1-10).

*Primary Examiner* — Colin T. Sakamoto
(74) *Attorney, Agent, or Firm* — Blueshift IP, LLC; Cynthia M. Gilbert

(57) ABSTRACT

A method for automated steering of magnetically steerable intravascular guidewires includes accessing, by a magnetic steering control component, volumetric imaging associated with a patient. The magnetic steering control component generates, prior to an operation on the patient, a three-dimensional vessel map based upon the accessed volumetric imaging. The magnetic steering control component generates, prior to the operation, a path through a vasculature of the patient. The magnetic steering control component displaying, prior to the operation, in a graphical user interface, the three-dimensional vessel map and the path. The magnetic steering control component receives input representing a modification to the path and modifies the path based upon the received input. The magnetic steering control component directs, during the operation, at least one of a medical robot arm and a motorized guidewire advancing unit to modify a location of a magnetically steerable intravascular guidewire in accordance with the modified path.

21 Claims, 15 Drawing Sheets

(51) Int. Cl.

*A61B 34/10* (2016.01)
*A61B 34/30* (2016.01)
*A61M 25/09* (2006.01)

(52) U.S. Cl.

CPC ............. *A61B 34/30* (2016.02); *A61M 25/09* (2013.01); *A61B 2034/105* (2016.02); *A61B 2034/107* (2016.02); *A61B 2034/254* (2016.02); *A61B 2034/301* (2016.02); *A61M 25/09041* (2013.01); *A61M 2025/09175* (2013.01)

(56) References Cited

U.S. PATENT DOCUMENTS

| | | | | |
|---|---|---|---|---|
| 10,583,269 | B2 | 3/2020 | Burkholz | |
| 11,103,324 | B2 | 8/2021 | Zhao | |
| 11,147,635 | B1 * | 10/2021 | Sganga | G16H 40/63 |
| 11,779,422 | B2 | 10/2023 | Zhao | |
| 12,246,144 | B2 | 3/2025 | Choi | |
| 2004/0019447 | A1 * | 1/2004 | Shachar | A61B 17/22 702/115 |
| 2005/0197566 | A1 * | 9/2005 | Strommer | A61B 5/06 600/424 |
| 2005/0256398 | A1 | 11/2005 | Hastings | |
| 2012/0035460 | A1 * | 2/2012 | Stangenes | A61B 5/062 604/95.01 |
| 2012/0035539 | A1 * | 2/2012 | Tegg | A61M 25/0127 606/41 |
| 2017/0296277 | A1 | 10/2017 | Hourtash | |
| 2017/0325894 | A1 * | 11/2017 | Krimsky | A61B 18/1492 |
| 2021/0386497 | A1 | 12/2021 | Zhao | |
| 2022/0160999 | A1 * | 5/2022 | Choi | A61M 25/0158 |
| 2022/0202506 | A1 | 6/2022 | Sganga | |
| 2023/0138992 | A1 | 5/2023 | Pietro | |
| 2023/0320801 | A1 | 10/2023 | Wang | |
| 2023/0346507 | A1 | 11/2023 | Lang | |
| 2023/0380921 | A1 | 11/2023 | Dreyfus | |
| 2024/0130796 | A1 * | 4/2024 | Song | A61B 34/20 |
| 2025/0040989 | A1 * | 2/2025 | Voncken | G16H 50/50 |

FOREIGN PATENT DOCUMENTS

| | | | | | |
|---|---|---|---|---|---|
| CN | 116196099 | A | * | 6/2023 | G06T 5/20 |
| KR | 102305965 | B1 | * | 9/2021 | G06T 7/248 |
| KR | 20240035632 | A | | 3/2024 | |
| WO | 2023219964 | A1 | | 11/2023 | |
| WO | WO-2024251719 | A1 | * | 12/2024 | A61B 17/12186 |

* cited by examiner

Magnetic Steering Control Component 103

GUI 117

Physical Interface Component 115

Medical Robot Arm 105

Remote-Control Console 111

Joystick 113

Magnetically Steerable Intravascular Guidewire 107

Motorized Guidewire and Catheter Advancing Unit 109

100

100

METHODS AND SYSTEMS FOR AUTOMATED STEERING OF GUIDEWIRES

CROSS-REFERENCE TO RELATED APPLICATIONS

This application claims priority to U.S. Provisional Patent Application Ser. No. 63/701,693, filed on Oct. 1, 2024, entitled, "Methods and Systems for Automated Steering of Guidewires," which is hereby incorporated by reference.

BACKGROUND

The disclosure relates to methods and system for steering guidewires. More particularly, the methods and systems described herein relate to functionality for automated steering of magnetically steerable intravascular guidewires.

Magnetically steerable intravascular guidewires have shown promise in addressing navigational challenges within complex vascular anatomies. Such guidewires can be deflected on demand under the influence of externally applied magnetic fields, enabling directional steering of the guidewire tip. When steering is achieved by adjusting the spatial position and orientation of an external magnetic source relative to the guidewire tip within a patient's vasculature, it is necessary to determine the appropriate alignment of the magnetic source to produce the desired deflection. To ensure practical usability, the control of magnetic steering based on user input should be performed automatically, thereby reducing operator workload and cognitive burden.

Therefore, there is a need for technological improvements to systems and methods for using magnetically steerable intravascular guidewires.

BRIEF SUMMARY

In one aspect, a method for automated steering of magnetically steerable intravascular guidewires includes accessing, by a magnetic steering control component, volumetric imaging associated with a patient. The method includes generating, prior to an operation on the patient, by the magnetic steering control component, a three-dimensional vessel map based upon the accessed volumetric imaging. The method includes generating, prior to the operation, by the magnetic steering control component, a path from an initial point in a vasculature of the patient to a target location in the vasculature, based upon the generated three-dimensional vessel map. The method includes displaying, prior to the operation, by the magnetic steering control component, in a graphical user interface, the three-dimensional vessel map and the generated path. The method includes receiving, prior to the operation, by the magnetic steering control component, from the graphical user interface, input representing a modification to the generated path. The method includes modifying, prior to the operation, by the magnetic steering control component, the generated path based upon the received input. The method includes directing, during the operation, by the magnetic steering control component, at least one of a medical robot arm and a motorized guidewire advancing unit to modify a location of a magnetically steerable intravascular guidewire through the vasculature of the patient in accordance with the modified path.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION

The methods and systems described herein may provide functionality for automated steering of magnetically steerable intravascular guidewires. In some embodiments, implementations of the methods and systems described herein may provide improved precision, efficiency, and ease of use.

Figure 1A:
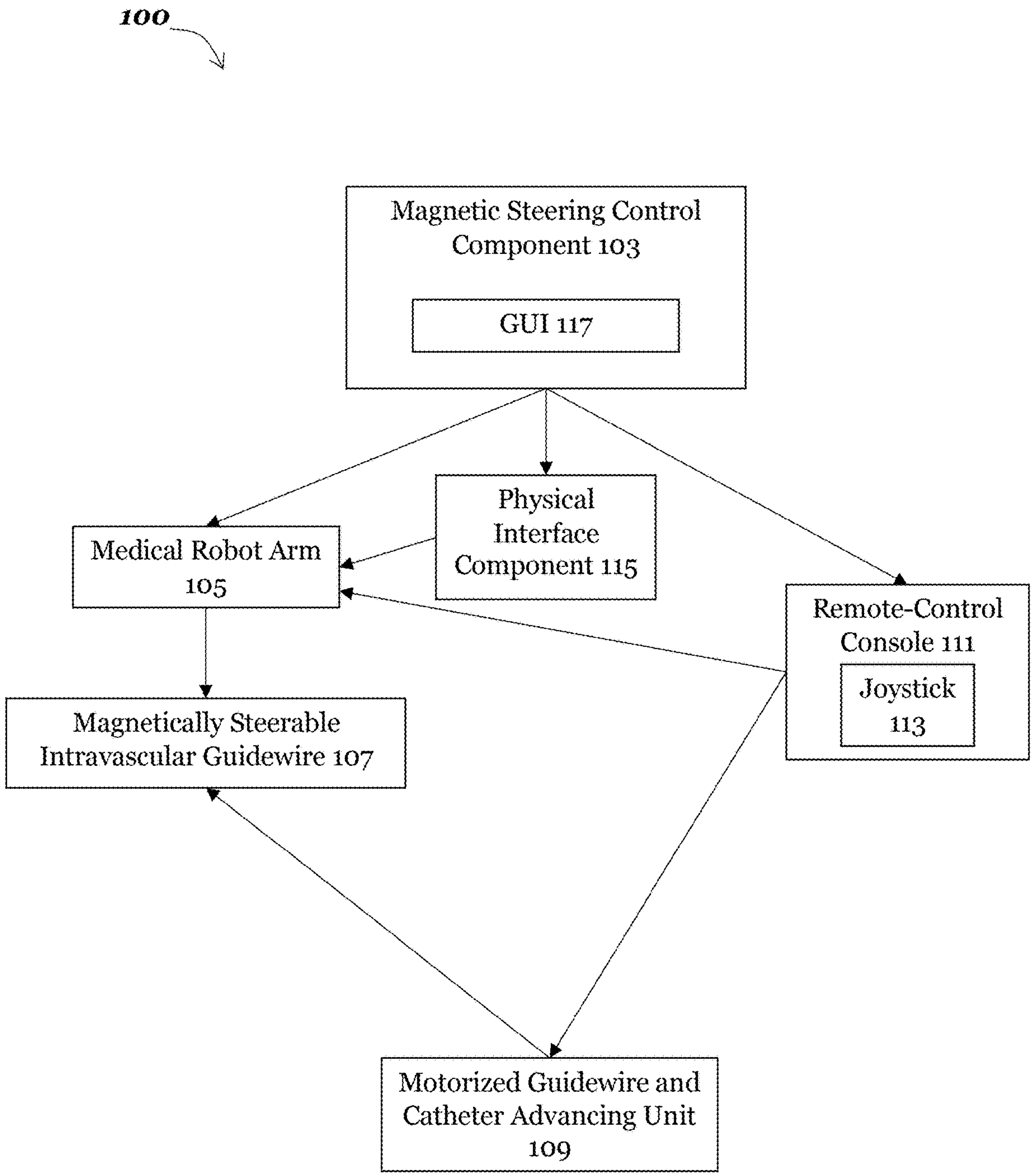
FIG. 1A is a block diagram depicting an embodiment of a magnetic robotic navigation (MRN) system.

Referring now to FIG. 1A, a block diagram depicts an embodiment of a magnetic robotic navigation (MRN) system 100. The system 100 includes a magnetic steering control component 103, a medical robot arm 105, a magnetically steerable intravascular guidewire 107, a motorized guidewire and catheter advancing unit 109, a remote-control console 111, a joystick 113, a physical interface component 115, and a graphical user interface 117.

In some embodiments, the MRN system 100 is used in robotically-assisted delivery and manipulation of magnetically steerable micro-guidewires, magnetically steerable diagnostic guidewires (0.035" or 0.038"), microcatheters, angiographic catheters, guide catheters, and other interventional devices (embolization coils, stent retrievers, aspiration catheters) during endovascular procedures (e.g., operations).

The system 100 includes a magnetically steerable intravascular guidewire 107, which may also be referred to herein as the guidewire 107. The magnetically steerable intravascular guidewire 107 may be a magnetic guidewire that has a steerable distal portion, which can be manipulated through spatial positioning of an actuating magnet at the end effector of the medical robot arm 105, relative to the steerable tip.

Figure 1B:
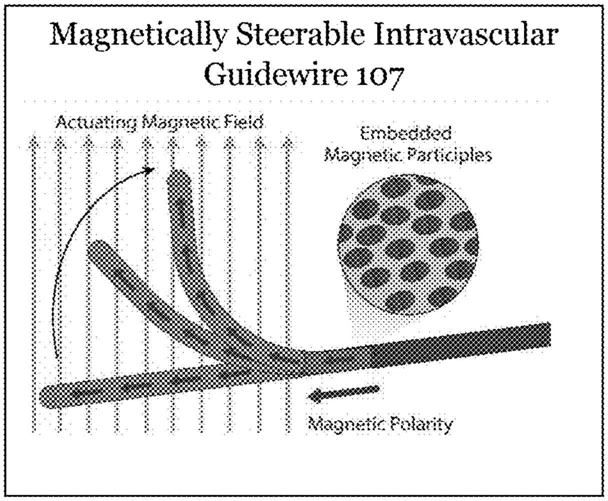
FIG. 1B is a block diagram depicting an embodiment of the magnetically steerable intravascular guidewire.

Referring now to FIG. 1B, a block diagram depicts one embodiment of the magnetically steerable intravascular guidewire 107. Unlike conventional "magnet-tipped" designs in which a finite-sized, rigid magnet is attached at the distal end of the wire, as shown in FIG. 1B, the magnetically steerable intravascular guidewire 107 may incorporate a "soft continuum" design based on polymer composites with evenly dispersed magnetic particles as distributed actuation sources.

Figure 1C:
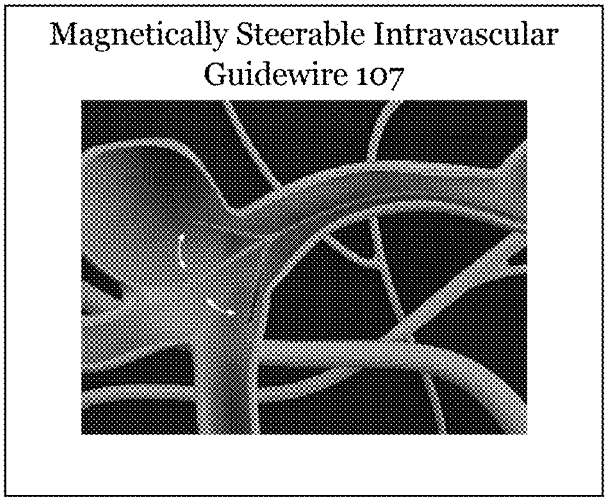
FIG. 1C is a block diagram depicting an embodiment of the magnetically steerable intravascular guidewire.

Referring ahead to FIG. 1C, a block diagram depicts one embodiment of the magnetically steerable intravascular guidewire 107 within vasculature. FIG. 1C provides an illustration of the magnetically steerable intravascular guidewire 107 positioned in (and enabled to navigate through) vasculature with an aneurysm. As shown in FIG. 1C, the magnetic particles may generate magnetic torques and forces in the presence of an external magnetic field for steering purposes. The magnetic particles embedded in the polymer jacket are magnetized along the guidewire's axial direction, so the guidewire tip behaves essentially as a flexible permanent magnet. When an external magnetic field is applied, the magnetic torques generated by the distributed magnetized particles collectively lead to macroscale material response in the form of torque-driven bending actuation of the guidewire tip to create omnidirectional steering of the guidewire tip.

Referring back to FIG. 1A, the system 100 includes medical robot arm 105. The medical robot arm 105 may be a medical robot arm, such as, without limitation, a robotic arm as provided by KUKA Aktiengesellschaft of Augsburg, Germany, with an actuating magnet. Unlike conventional, bulky, and costly magnetic navigation systems, the MRN system 100 may provide a mobile, compact, and lightweight robotic manipulation platform and incorporate a single robotic arm that holds a permanent magnet or an electromagnet. With its small mechanical footprint, the MRN system 100 is compatible with single-plane or bi-plane angiography suites for vascular interventions. Although spatial positioning of the magnet requires at five degrees of freedom (DOFs), the MRN system 100 uses a 7-DOF serial robot arm manipulator with seven revolute joints to take advantage of its kinematic redundancy for safer operation in cluttered environments with a confined workspace. The extra DOF provides an increased level of dexterity that helps the robot arm avoid singularities and joint limits as well as workspace obstacles.

The system 100 includes a magnetic steering control component 103. The magnetic steering control component 103 may also be referred to herein as a robot control component for automated magnetic steering. The magnetic steering control component 103 may generate, display, and/or modify a graphical user interface 117. The magnetic steering control component 103 may display visual feedback from real-time fluoroscopic imaging of one or more devices in the blood vessels.

Figure 1D:
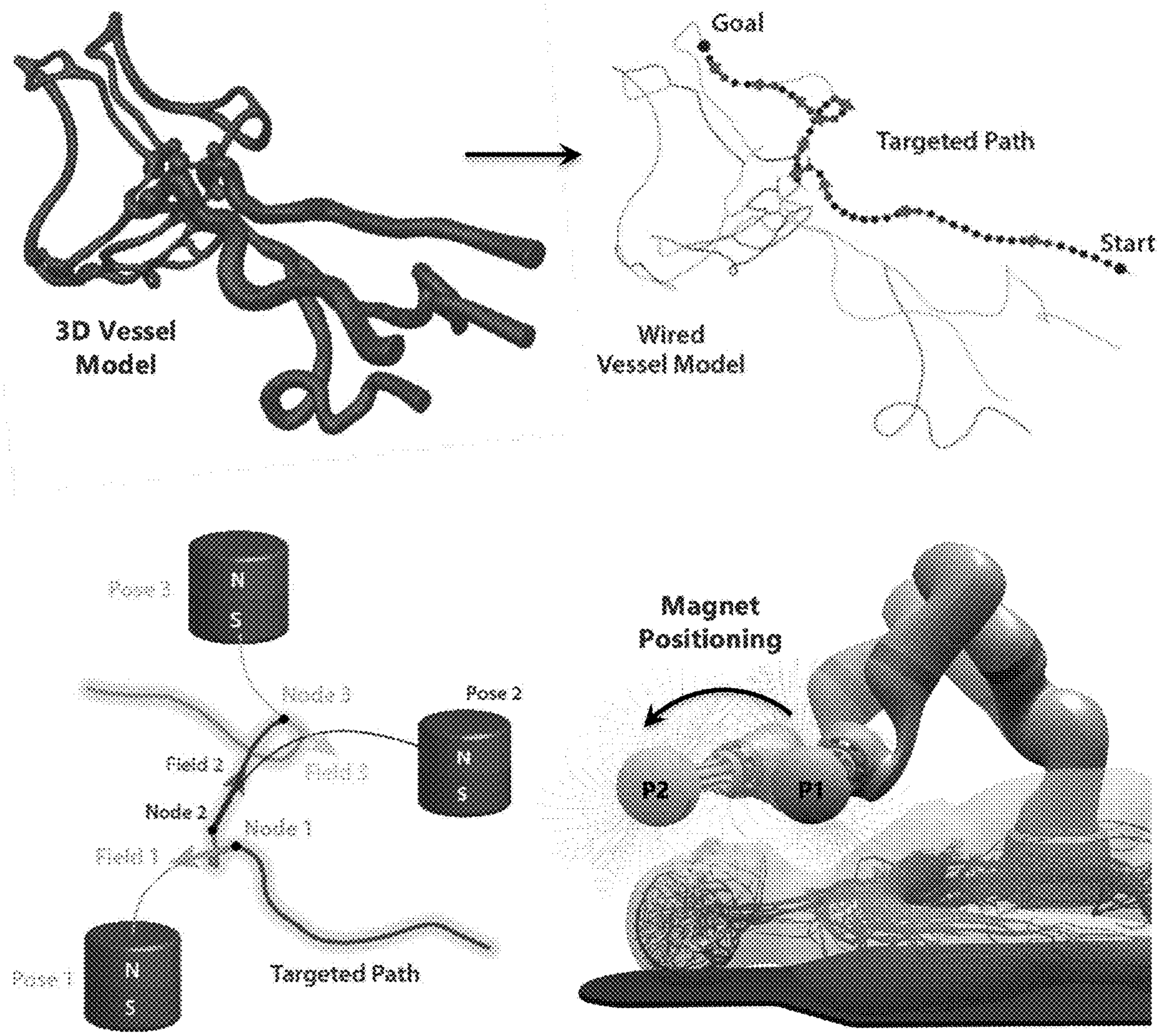
FIG. 1D is a block diagram depicting an embodiment of vessel models in an MRN system.

Referring now to FIG. 1D, a block diagram depicts one embodiment of a vessel model in the MRN system 100. The magnetic steering control component 103 may generate and display a 3D reconstructed model of a target vasculature (obtained, for example, from pre-operative imaging such as CT or MR angiography or intraoperative imaging such as 3D rotational angiography) in the graphical user interface 117. The operator may select a targeted path to navigate and specify the desired steering directions at each critical location (e.g., sharp corners, bifurcation points) ahead of the operation.

Figure 1E:
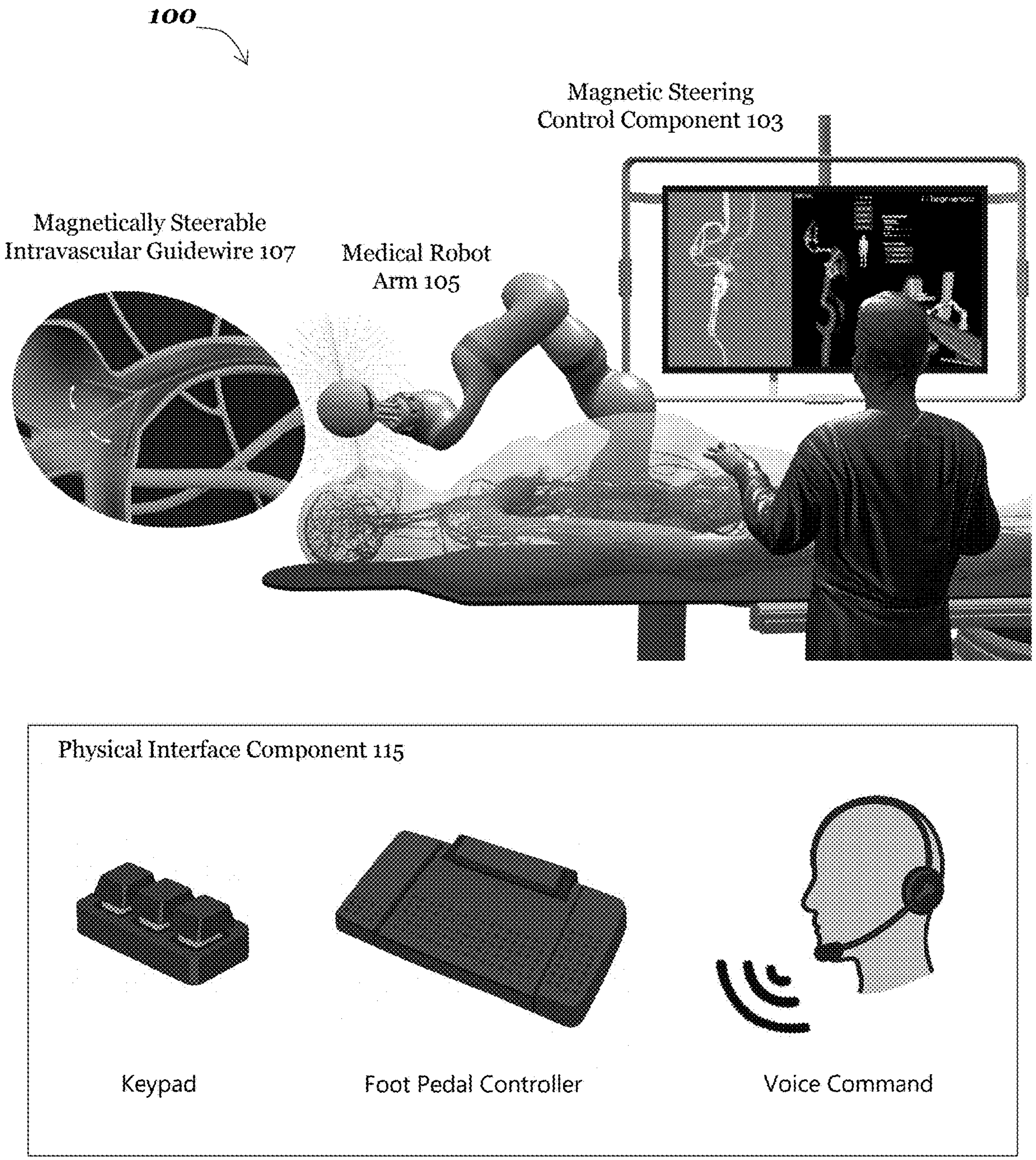
FIG. 1E is a block diagram depicting an embodiment of an MRN system.
Figure 1F:
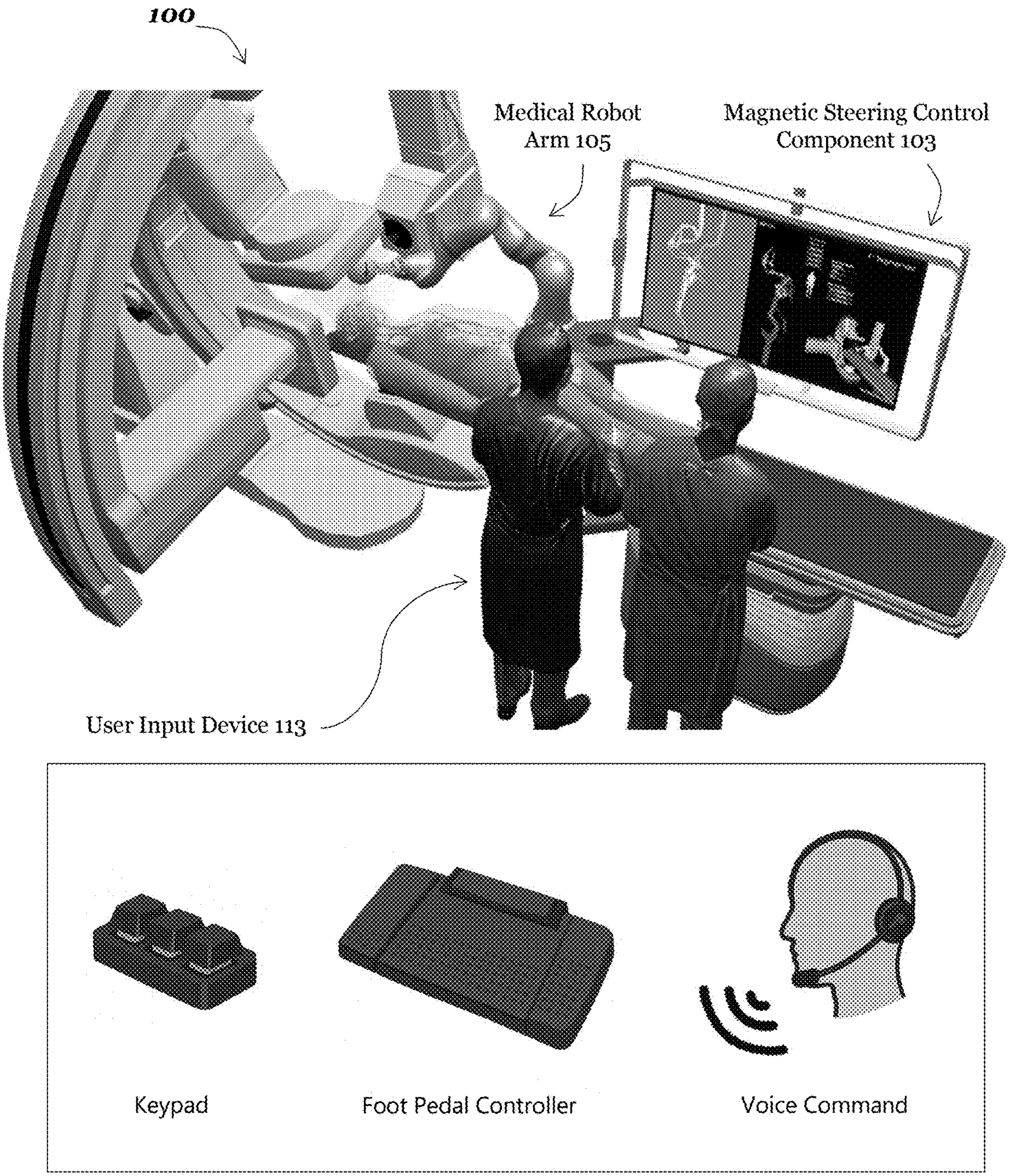
FIG. 1F is a block diagram depicting an embodiment of an MRN system deployed in a biplane angiography suite.
Figure 1G:
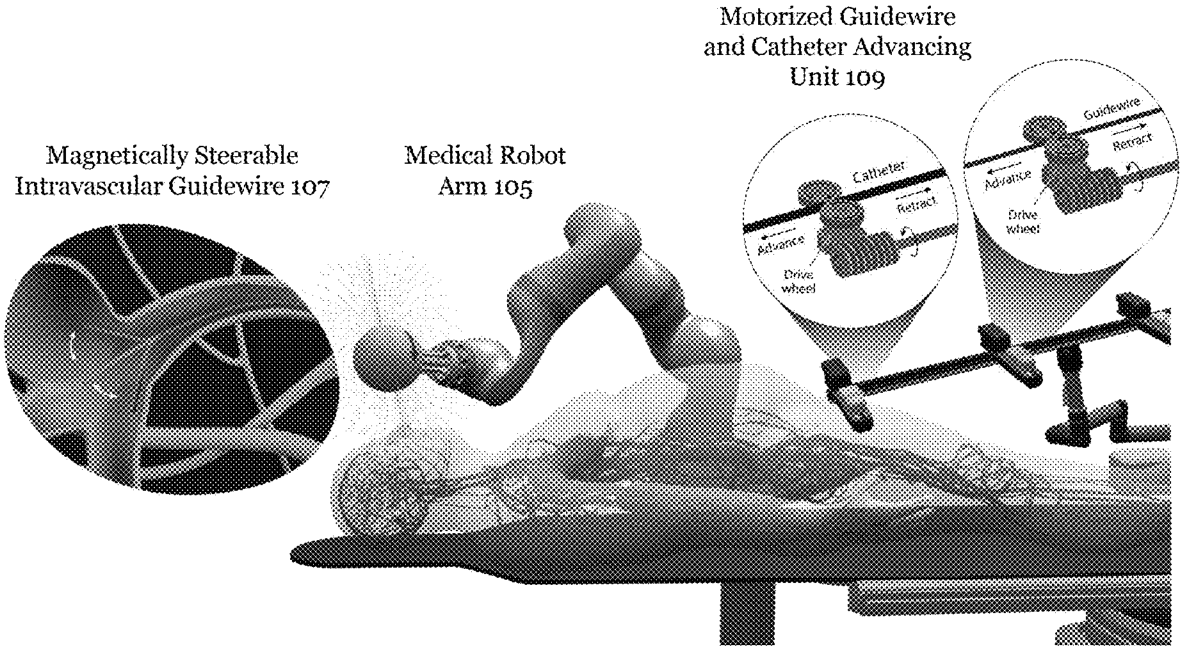
FIG. 1G is a block diagram depicting an embodiment of an MRN system including a motorized guidewire and catheter advancing unit.
Figure 1G:
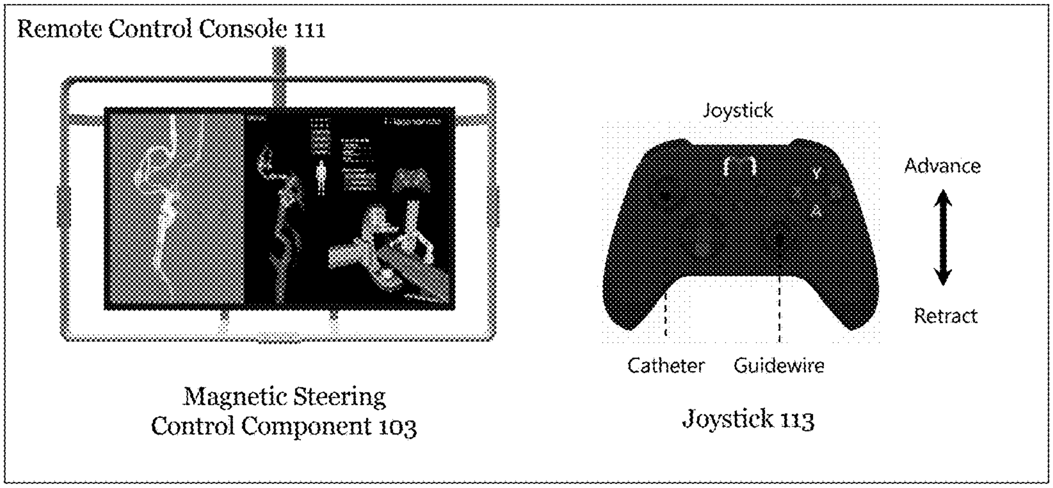
Figure 1H:
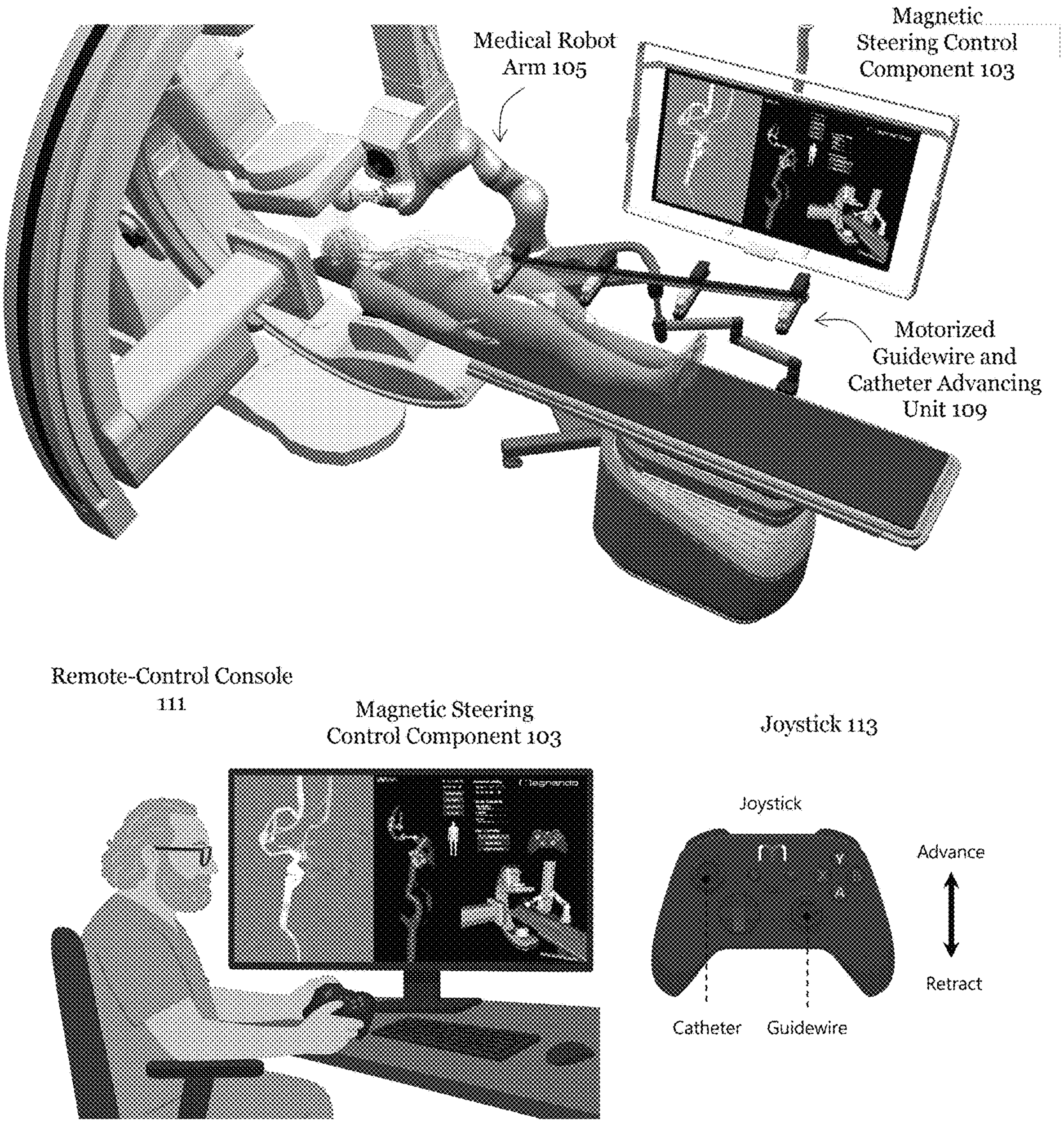
FIG. 1H is a block diagram depicting an embodiment of an MRN system deployed in a biplane angiography suite and including a motorized guidewire and catheter advancing unit.

Referring back to FIG. 1A and in connection with FIG. 1H, in some embodiments, the system 100 allows an operator to work remotely from a patient table and a radiation source (C-arm) in a separate control room in which the remote-control console 111 is installed. In such embodiments, the remote-control console 111 (which may also be referred to as a control workstation) may display the graphical user interface generated and/or displayed by the magnetic steering control component 103. The remote-control console 111 may include or be in communication with a joystick 113. In other embodiments, the remote-control console 111 is installed in the same room as the patient table the system 100 allows a user to work physically proximate to the patient table and use the remote-control console 111.

Figure 1I:
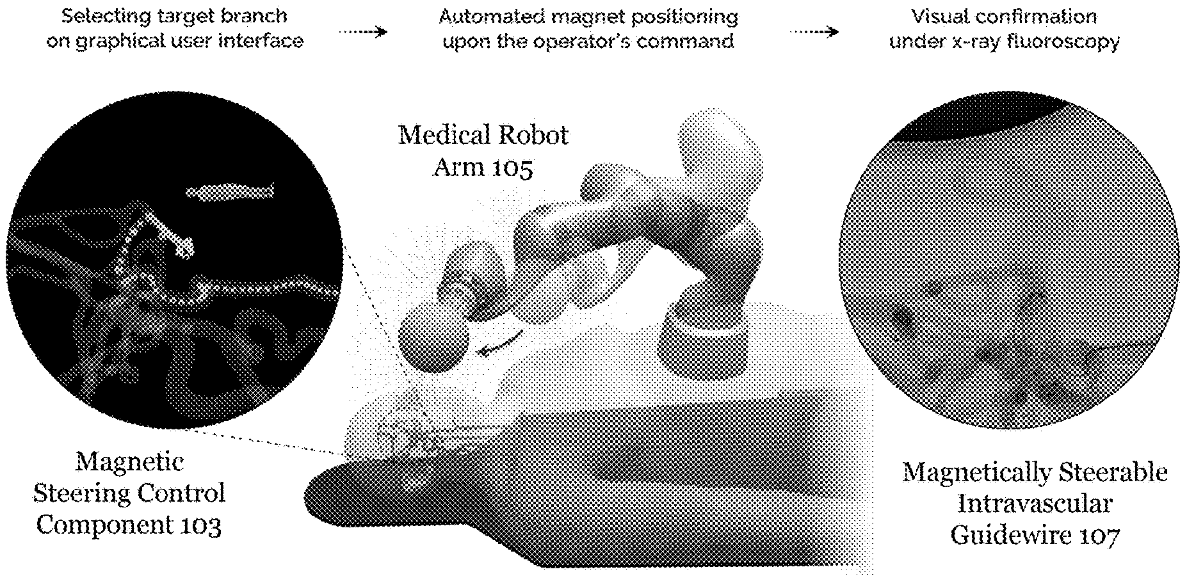
FIG. 1I is a block diagram depicting an embodiment of an MRN system.

Referring ahead to FIG. 1I, a block diagram depicts an embodiment of the system 100. As depicted in FIG. 1I, a user may interact with the system 100 while viewing visual feedback in the graphical user interface 117. Upon receiving a user's command (e.g., from the joystick 113 or the physical interface component 115), motion of the medical robot arm 105 is executed (e.g., the robot arm 105 reconfigures itself to change position and orientation) to spatially position the actuating magnet around the patient's head such that the applied magnetic field to the point of interest in the patient's vessels is aligned with the user-specified direction for steering the magnetic guidewire within the patient's blood vessels. The x-ray fluoroscopy may provide a real-time visualization of the magnetic guidewire being steered robotically and other interventional devices being manipulated. As shown in both FIGS. 1D and 1I, with embedded motion planning and optimization algorithms, the magnetic steering control component 103 may automatically calculate an optimal position and orientation of the actuating magnet around the patient and its joint configuration to achieve a magnet pose while avoiding collision with the surrounding objects (e.g., the patient, C-arms, operating table, and radiation shields). Therefore, in some embodiments, the method 200 described below may include executing, by the magnetic steering control component, at least one motion-planning and optimization algorithm, to automatically calculate (i) a position and orientation of an actuating magnet in proximity to the patient to generate a magnetic field that is aligned with a user-specified steering direction and (ii) a joint configuration of the medical robot arm 105 that corresponds to the calculated position and orientation of the actuating magnet. In such embodiments, executing the motion-planning and optimization algorithm may include executing the at least one motion-planning and optimization algorithm to automatically calculate a position and orientation of the actuating magnet that avoids collision with an object in proximity to the medical robot arm. In such embodiments, executing the motion-planning and optimization algorithm may include executing the at least one motion-planning and optimization algorithm to automatically calculate the joint configuration of the medical robot arm that corresponds to the calculated position and orientation of the actuating magnet and that avoids collision with an object in proximity to the medical robot arm. In such embodiments, executing the motion-planning and optimization algorithm may include automatically calculating a kinematic trajectory of the medical robot arm that avoids a collision with an object in proximity to the medical robot arm.

Upon confirmation of the wire tip orientation from real-time fluoroscopy, the user can further advance the magnetic guidewire (e.g., from the remote-control console via the joystick 113). Along with the magnetic guidewire, additional interventional devices (e.g., a microcatheter and a guide catheter) may be controlled either independently or simultaneously.

Referring back to FIG. 1A, the system 100 may include a motorized guidewire and catheter advancing unit 109. The motorized guidewire and catheter advancing unit 109 may include at least one motorized linear drives to advance or retract the magnetic guidewire and other interventional devices upon receiving commands. The motorized guidewire and catheter advancing unit 109 may receive commands from a remote-control console 111 via a joystick 113 in communication with the magnetic steering control component 103. As indicated above, in embodiments in which the user interacts with the physical interface component 115, the motorized guidewire and catheter advancing unit 109 may be optional.

As shown in FIG. 1G, the motorized guidewire and catheter advancing unit 109 may accommodate and manipulate a tri-axially or quadri-axially configured set of interventional devices (e.g., micro-guidewire, microcatheter, intermediate catheter, aspiration catheter, and/or guide catheter) simultaneously or independently under real-time joystick operation from the remote-control console 111. Because the system 100 utilizes magnetic steering for navigation instead of rotating a pre-shaped guidewire or catheter for steering purposes, it obviates the need to rotate the devices with pre-bent distal tips. Therefore, unlike other vascular robotic systems that utilize the combination of linear and rotational drives, the system 100 may include at least three linear drives, which significantly simplifies the mechanical design of the guidewire/catheter advancing unit 109. The advancing unit may include a pair of drive wheel and idler that may be engaged with the device (e.g., guidewire or catheter) being advanced or retracted upon the rotation of the drive wheel.

Referring still to FIG. 1A, and in some embodiments, instead of using the remote-control console 111, a user of the system 100 is physically proximate to the medical robot arm 105 and to a physical interface component 115. In such embodiments, both the remote-control console 111 and the motorized guidewire and catheter advancing unit 109 are optional. Instead, the graphical user interface 117 displays directions to the user of the physical interface component 115 and the user interacts with the physical interface component 115 to manipulate the medical robot arm 105. In such an embodiment, the user may physically move the magnetically steerable intravascular guidewire 107. The physical interface component 115 may include interface elements such as a keypad, footswitch, and/or voice activated controller.

Referring now to FIG. 1E, a block diagram depicts an embodiment of an MRN system 100 in which the user interacts with the physical interface component 115 instead of with the remote-control console 111. FIG. 1E depicts a view of the magnetic steering control component 103, the medical robot arm 105, the magnetically steerable intravascular guidewire 107, and the physical interface component 115. The physical interface component 115 may include a keypad. The physical interface component 115 may include a foot pedal controller. The physical interface component 115 may include a voice command interface. The user may manually advance the magnetically steerable intravascular guidewire 107.

Referring now to FIG. 1F, a block diagram depicts an embodiment of an MRN system deployed in a biplane angiography suite, in which a user manually advances the magnetically steerable intravascular guidewire 107 while the MRN system 100 provides robotically controlled automated steering. FIG. 1F provides an overview of the MRN system 100 deployed in a clinical setting for image-guided intravascular interventions, with biplane C-arm fluoroscopy machines providing real-time imaging of a patient's vasculature and the guidewire 107 navigating in the blood vessels via user manipulation. Mounted on a mobile platform beside the operating table, the medical robot arm 105 with an actuating magnet may be flexibly arranged within the operating room.

Figure 2:
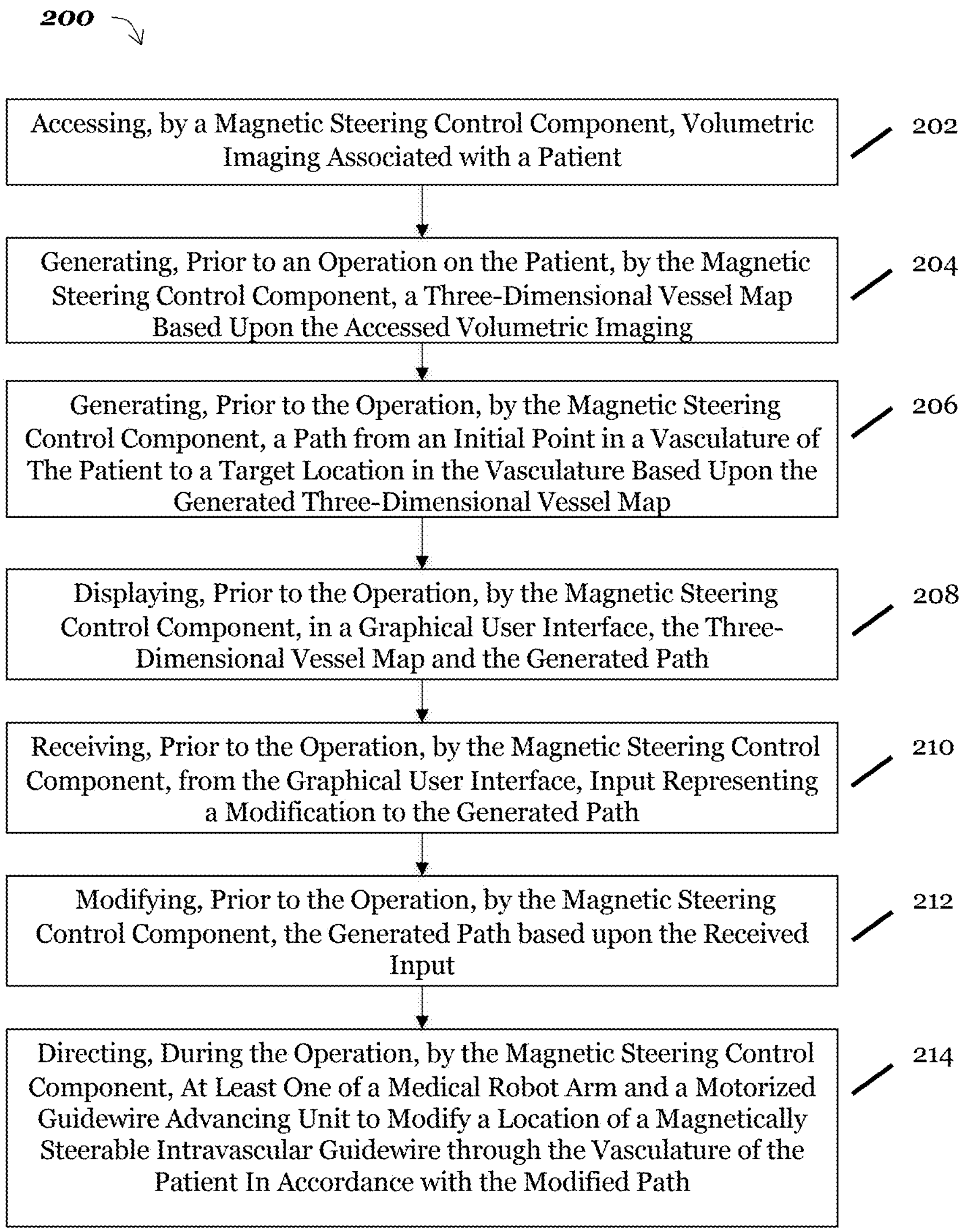
FIG. 2 is a flow diagram depicting an embodiment of a method for automated steering of magnetically steerable intravascular guidewire.

Referring now to FIG. 2, in brief overview, a flow diagram depicts one embodiment of a method 200 for automated steering of a magnetically steerable intravascular guidewire. The method 200 includes accessing, by a magnetic steering control component, volumetric imaging associated with a patient (202). The method 200 includes generating, prior to an operation on the patient, by the magnetic steering control component, a three-dimensional vessel map based upon the accessed volumetric imaging (204). The method 200 includes generating, prior to the operation, by the magnetic steering control component, a path from an initial point in a vasculature of the patient to a target location in the vasculature, based upon the generated three-dimensional vessel map (206). The method 200 includes displaying, prior to the operation, by the magnetic steering control component, in a graphical user interface, the three-dimensional vessel map and the generated path (208). The method 200 includes receiving, prior to the operation, by the magnetic steering control component, from the graphical user interface, input representing a modification to the generated path (210). The method 200 includes modifying, prior to the operation, by the magnetic steering control component, the generated path based upon the received input (212). The method 200 includes directing, during the operation, by the magnetic steering control component, at least one of a medical robot arm and a motorized guidewire advancing unit to modify a location of a magnetically steerable intravascular guidewire through the vasculature of the patient in accordance with the modified path (214).

Referring now to FIG. 2, in greater detail and in connection with FIG. 1, the method 200 for automated steering of a magnetically steerable intravascular guidewire includes accessing, by a magnetic steering control component, volumetric imaging associated with a patient (202). In some embodiments, the magnetic steering control component 103 accesses the volumetric imaging. The volumetric imaging may be, by way of example and without limitation, a computed tomography scan, a computed tomography (CT) angiogram scan, a cone beam computed topography image, a magnetic resonance angiogram, or other volumetric imaging.

The method 200 includes generating, prior to an operation on the patient, by the magnetic steering control component, a three-dimensional vessel map based upon the accessed volumetric imaging (204). The magnetic steering control component 103 may access scans associated with the patient to generate and/or refine the three-dimensional vessel map. The magnetic steering control component 103 may modify the volumetric image to generate the three-dimensional image. The magnetic steering control component 103 may modify the volumetric imaging prior to generating the three-dimensional image; for example, the magnetic steering control component 103 may remove portions of the volumetric imaging that need not be represented in the three-dimensional image.

The method 200 includes generating, prior to the operation, by the magnetic steering control component, a path from an initial point in a vasculature of the patient to a target location in the vasculature, based upon the generated three-dimensional vessel map (206). The magnetic steering control component 103 may access data associated with a type of the operation in generating the path; the magnetic steering control component 103 may use the accessed data to generate the path. The magnetic steering control component 103 may access data associated with one or more electronic health records of the patient in generating the path.

The method 200 includes displaying, prior to the operation, by the magnetic steering control component, in a graphical user interface, the three-dimensional vessel map and the generated path (208). The magnetic steering control component 103 may modify the graphical user interface to identify at least one branch in the vasculature along the path that the magnetically steerable intravascular guidewire 107 will navigate during the operation. The magnetic steering control component 103 may generate and display a graphical user interface element within the graphical user interface identifying a node along the path at which a vessel branches and where the magnetically steerable intravascular guidewire 107 will need to navigate the branch during the operation.

The method 200 may include modifying the graphical user interface during the operation. In some embodiments, as the x-ray fluoroscopy provides real-time visualization of the magnetic guidewire, the system 100 may modify the graphical user interface. By way of example, the magnetic steering control component 103, may use data received from the x-ray fluoroscopy to modify a display of the graphical user interface element identifying the node along the path as displaying the next branch at which the guidewire 107 may change direction. By way of example, and without limitation, the magnetic steering control component 103 may modify a color or other visual characteristic of the user interface element identifying the node as the next branch. The magnetic steering control component 103 may mark a portion of the graphical user interface as displaying a previously navigated branch—for example, by changing a color of the graphical user interface to indicate that the marked portion has already been navigated (e.g., by greying out that portion or removing the marked portion from display in the graphical user interface). Such modifications to the graphical user interface reduce cognitive burdens on the users and, therefore, reduce the risk of errors.

Therefore, the method 200 may include modifying the graphical user interface to include a display of a first graphical user interface element identifying a first node in a plurality of nodes on the generated path, wherein each node in the plurality of nodes represents a location on the generated path at which there is a branch in the vessel map and through which the magnetically steerable intravascular guidewire will navigate during the operation. The method 200 may include modifying a visual characteristic of the first graphical user interface element identifying the first node to indicate that the first node is an upcoming node in the plurality of nodes on the generated path. The method 200 may include modifying the graphical user interface to include a display of a second graphical user interface element identifying a second node that is at an upcoming location along the path at which the vessel branches (e.g., at a location along the path subsequent to the first node). The method 200 may include modifying the graphical user interface to remove the display of the first graphical user interface element subsequent to navigation to the second node by the magnetically steerable intravascular guidewire. The method 200 may include modifying a visual characteristic of a graphical user interface element representing the first node subsequent to navigation by the magnetically steerable intravascular guidewire to the second node. In an embodiment in which the method 200 includes modifying a visual characteristic in a display of the graphical user interface element subsequent to navigation to the second node by the magnetically steerable intravascular guidewire, if user input is received indicating that the magnetically steerable intravascular guidewire is to return to the first node, the method 200 may include modifying the graphical user interface to reverse the modification of the visual characteristic of the graphical user interface element identifying the first node (e.g., to reintroduce the graphical user interface element if it was deleted or to reverse a modification of the visual characteristic).

The method 200 includes receiving, prior to the operation, by the magnetic steering control component, from the graphical user interface, input representing a modification to the generated path (210). The magnetic steering control component 103 may receive user input via the graphical user interface element identifying a direction for the magnetically steerable intravascular guidewire 107 to take at a branch in the vasculature; by way of example, and without limitation, the branch may be represented as a node on the path. The magnetic steering control component 103 may receive user input identifying a modification to the generated path at the node; for example, the user input may identify a specific direction for the magnetically steerable intravascular guidewire 107 to take at the branch that differs from a direction included in the generated path. Alternatively, the magnetic steering control component 103 may receive user input confirming the direction identified by the generated path at the node without requesting a modification. The method 200 may include receiving, prior to operation, by the magnetic steering control component, user input identifying a steering intention at one or more critical locations along the path, including bifurcations, branching points, and sharp turns. In such an embodiment, the user input may include an identification of a node selected by the user in the graphical user interface. In another such embodiment, the user input may include an identification of a desired branch direction.

The method 200 includes modifying, prior to the operation, by the magnetic steering control component, the generated path based upon the received input (212). Upon receiving user input, the magnetic steering control component 103 may confirm or modify the generated path.

The method 200 includes directing, during the operation, by the magnetic steering control component, at least one of a medical robot arm and a motorized guidewire advancing unit to modify a location of a magnetically steerable intravascular guidewire through the vasculature of the patient in accordance with the modified path (214). The magnetic steering control component 103 may transmit at least one direction to the medical robot arm 105 in a format processable by the medical robot arm 105. The magnetic steering control component 103 may transmit at least one direction to the motorized guidewire and catheter advancing unit 109 in a format processable by the motorized guidewire and catheter advancing unit 109.

In some embodiments, the method 200 may include displaying at least one direction to a user in the graphical user interface and the user may use a physical interface component to issue commands to move the robot arm 105. For example, the user may interact with a physical interface component such as a keypad, a footswitch, a joystick, or a voice-activated controller. The method may include directing the user to interact with a physical interface component to modify the location of the magnetically steerable intravascular guidewire.

The method 200 may include displaying, during the operation, the graphical user interface displaying the three-dimensional vessel map and the generated path. The method 200 may include receiving, during the operation, from the graphical user interface, input representing a modification to the generated path. The method 200 may include modifying, during the operation, the generated path based upon the received input.

In some embodiments, the method 200 includes receiving additional volumetric imaging during the operation; analyzing the received additional volumetric imaging; and modifying the generated path during the operation. For example, the magnetic steering control component 103 may receive intra-operatively acquired volumetric imaging such as, without limitation, three-dimensional rotational angiograms taken by the C-arm imager and the magnetic steering control component 103 may modify the path generated from the pre-operative imaging based upon an analysis of the received intra-operatively acquired volumetric imaging.

Figure 3:
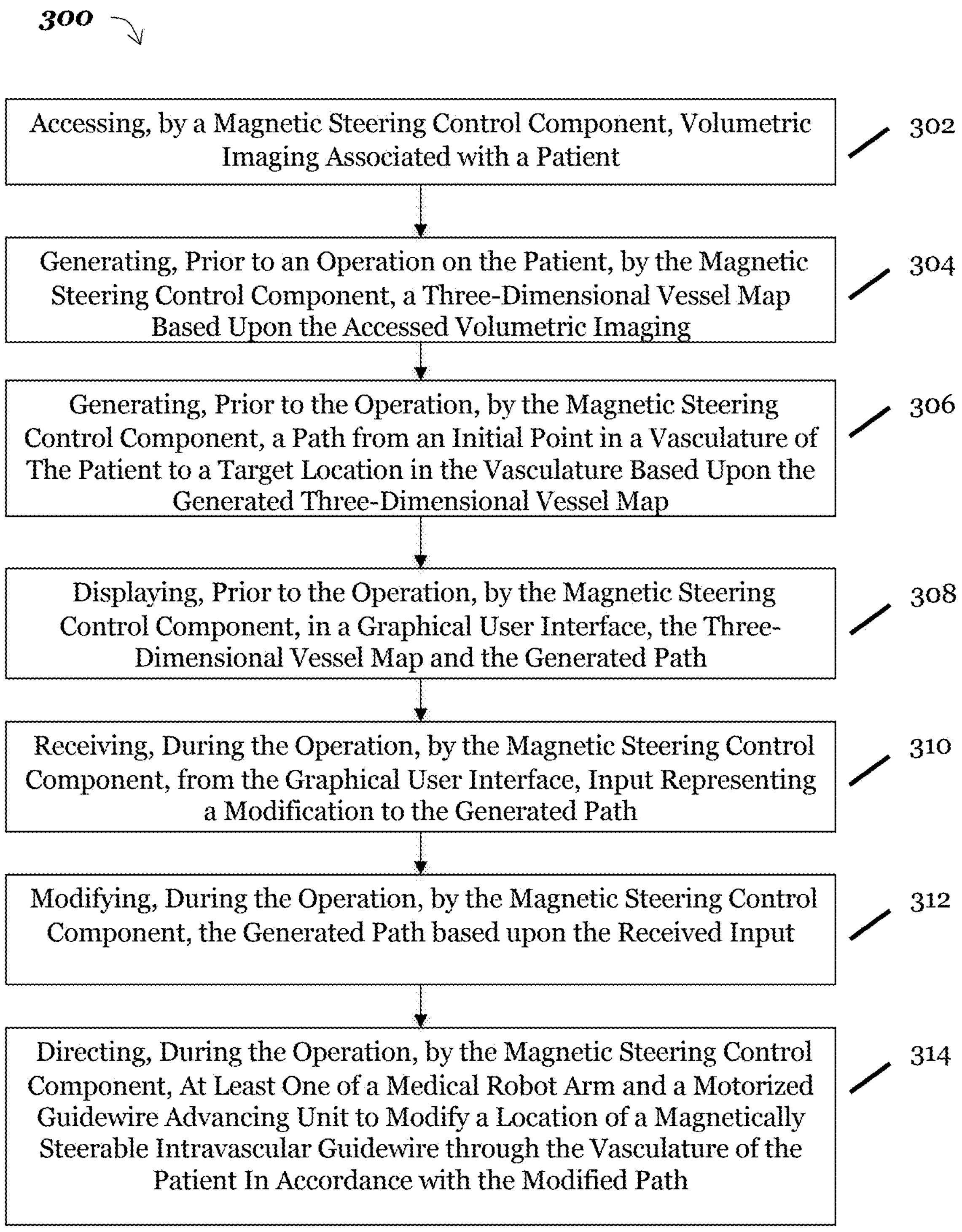
FIG. 3 is a flow diagram depicting an embodiment of a method for automated steering of magnetically steerable intravascular guidewire.

Although FIG. 2 above describes embodiments in which the modification to the generated path occurs before the operation, the modification may occur during the operation as well as, or instead of, occurring before the operation. Referring now to FIG. 3, in brief overview, a flow diagram depicts one embodiment of a method 300 for automated steering of a magnetically steerable intravascular guidewire that includes accessing, by a magnetic steering control component, volumetric imaging associated with a patient (302). The method 300 includes generating, prior to an operation on the patient, by the magnetic steering control component, a three-dimensional vessel map based upon the accessed volumetric imaging (304). The method 300 includes generating, prior to the operation, by the magnetic steering control component, a path from an initial point in a vasculature of the patient to a target location in the vasculature, based upon the generated three-dimensional vessel map (306). The method 300 includes displaying, prior to the operation, by the magnetic steering control component, in a graphical user interface, the three-dimensional vessel map and the generated path (308). The method 300 includes receiving, during the operation, by the magnetic steering control component, from the graphical user interface, input representing a modification to the generated path (310). The method 300 includes modifying, during the operation, by the magnetic steering control component, the generated path based upon the received input (312). The method 300 includes directing, during the operation, by the magnetic steering control component, at least one of a medical robot arm and a motorized guidewire advancing unit to modify a location of a magnetically steerable intravascular guidewire through the vasculature of the patient in accordance with the modified path (314).

Referring now to FIG. 3, in greater detail overview, the method 300 for automated steering of a magnetically steerable intravascular guidewire includes accessing, by a magnetic steering control component, volumetric imaging associated with a patient (302). The accessing may occur as described above in connection with FIG. 2 at (202).

The method 300 includes generating, prior to an operation on the patient, by the magnetic steering control component, a three-dimensional vessel map based upon the accessed volumetric imaging (304). The generating of the three-dimensional vessel map may occur as described above in connection with FIG. 2 at (204).

The method 300 includes generating, prior to the operation, by the magnetic steering control component, a path from an initial point in a vasculature of the patient to a target location in the vasculature, based upon the generated three-dimensional vessel map (306). The generating of the path may occur as described above in connection with FIG. 2 at (206).

The method 300 includes displaying, prior to the operation, by the magnetic steering control component, in a graphical user interface, the three-dimensional vessel map and the generated path (308). The displaying may occur as described above in connection with FIG. 2 at (208).

The method 300 includes receiving, during the operation, by the magnetic steering control component, from the graphical user interface, input representing a modification to the generated path (310). The receiving may occur as described above in connection with FIG. 2 at (210). Instead of receiving the input before the operation, however, in some embodiments, and as shown in FIG. 3, the input received at (310) may be received during the operation.

The method 300 includes modifying, during the operation, by the magnetic steering control component, the generated path based upon the received input (312). The modifying may occur as described above in connection with FIG. 2 at (212). Instead of modifying the path before the operation, however, in some embodiments, and as shown in FIG. 3, the modification may occur during the operation.

The method 300 includes directing, during the operation, by the magnetic steering control component, at least one of a medical robot arm and a motorized guidewire advancing unit to modify a location of a magnetically steerable intravascular guidewire through the vasculature of the patient in accordance with the modified path (314).

Referring now to FIG. 3, in greater detail overview, the method 300 for automated steering of magnetically steerable intravascular guidewire includes accessing, by a magnetic steering control component, volumetric imaging associated with a patient (302). The accessing may occur as described above in connection with FIG. 2 at (202).

The method 300 includes generating, prior to an operation on the patient, by the magnetic steering control component, a three-dimensional vessel map based upon the accessed volumetric imaging (304). The generating of the three-dimensional vessel map may occur as described above in connection with FIG. 2 at (204).

The method 300 includes generating, prior to the operation, by the magnetic steering control component, a path from an initial point in a vasculature of the patient to a target location in the vasculature, based upon the generated three-dimensional vessel map (306). The generating of the path may occur as described above in connection with FIG. 2 at (206).

Figure 4:
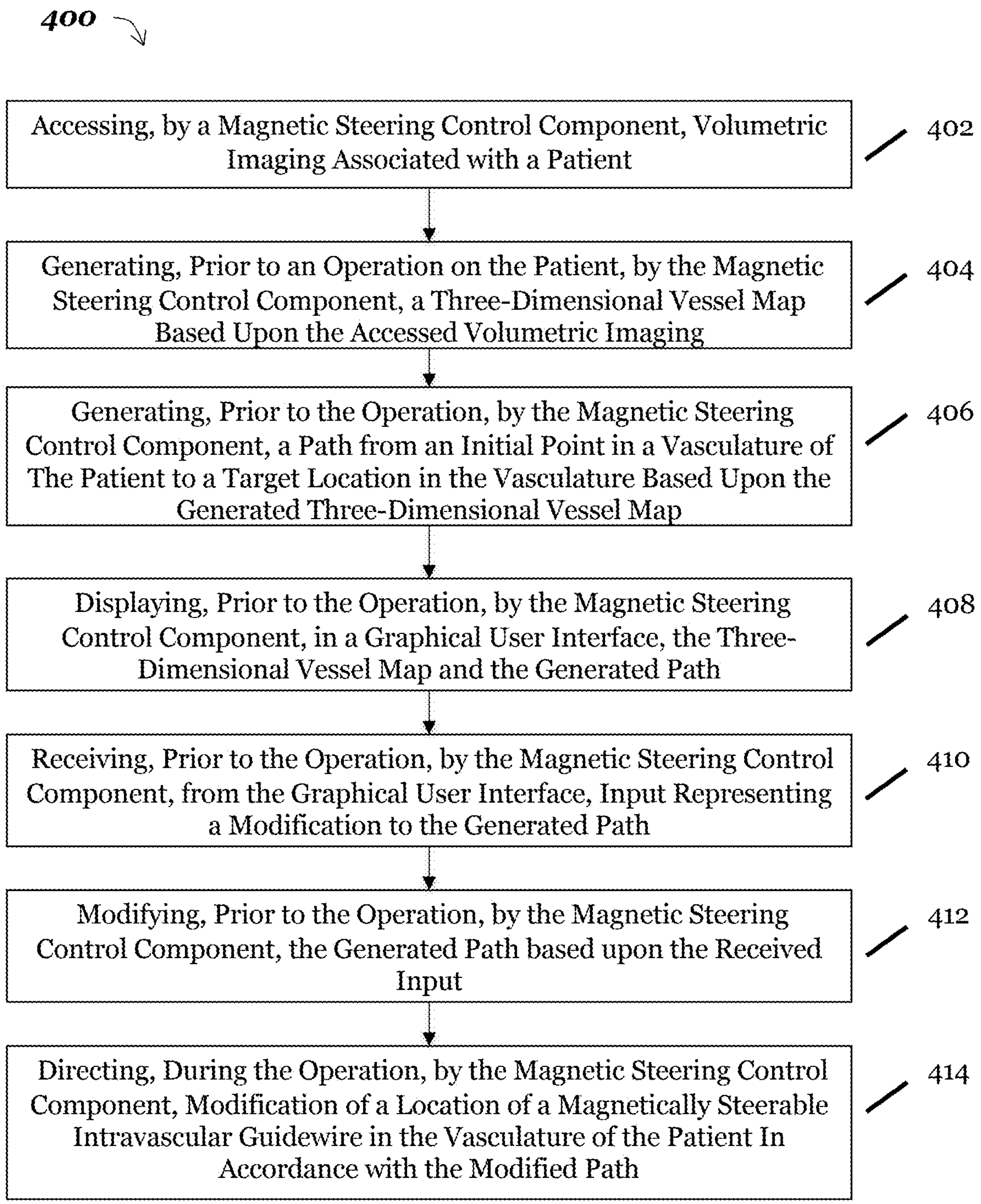
FIG. 4 is a flow diagram depicting an embodiment of a method for automated steering of magnetically steerable intravascular guidewire.

As indicated above, in some embodiments, it is optional to use the advancing unit 109. Referring now to FIG. 4, in brief overview, a flow diagram depicts one embodiment of a method 400 for automated steering of a magnetically steerable intravascular guidewire that includes accessing, by a magnetic steering control component, volumetric imaging associated with a patient (402). The method 400 includes generating, prior to an operation on the patient, by the magnetic steering control component, a three-dimensional vessel map based upon the accessed volumetric imaging (404). The method 400 includes generating, prior to the operation, by the magnetic steering control component, a path from an initial point in a vasculature of the patient to a target location in the vasculature, based upon the generated three-dimensional vessel map (406). The method 400 includes displaying, prior to the operation, by the magnetic steering control component, in a graphical user interface, the three-dimensional vessel map and the generated path (408). The method 400 includes receiving, during the operation, by the magnetic steering control component, from the graphical user interface, input representing a modification to the generated path (410). The method 400 includes modifying, during the operation, by the magnetic steering control component, the generated path based upon the received input (412). The method 400 includes directing, during the operation, by the magnetic steering control component, modification of a location of a magnetically steerable intravascular guidewire in the vasculature of the patient in accordance with the modified path (414).

Referring now to FIG. 4, in greater detail overview, the method 400 for automated steering of magnetically steerable intravascular guidewire includes accessing, by a magnetic steering control component, volumetric imaging associated with a patient (402). The accessing may occur as described above in connection with FIG. 2 at (202).

The method 400 includes generating, prior to an operation on the patient, by the magnetic steering control component, a three-dimensional vessel map based upon the accessed volumetric imaging (404). The generating of the three-dimensional vessel map may occur as described above in connection with FIG. 2 at (204).

The method 400 includes generating, prior to the operation, by the magnetic steering control component, a path from an initial point in a vasculature of the patient to a target location in the vasculature, based upon the generated three-dimensional vessel map (406). The generating of the path may occur as described above in connection with FIG. 2 at (206).

The method 400 includes displaying, prior to the operation, by the magnetic steering control component, in a graphical user interface, the three-dimensional vessel map and the generated path (408). The displaying may occur as described above in connection with FIG. 2 at (208).

The method 400 includes receiving, during the operation, by the magnetic steering control component, from the graphical user interface, input representing a modification to the generated path (410). The receiving may occur as described above in connection with FIG. 2 at (210). The receiving may occur as described above in connection with FIG. 3 at (310).

The method 400 includes modifying, during the operation, by the magnetic steering control component, the generated path based upon the received input (412). The modifying may occur as described above in connection with FIG. 2 at (212). The modifying may occur as described above in connection with FIG. 3 at (312).

The method 400 includes directing, during the operation, by the magnetic steering control component, modification of a location of a magnetically steerable intravascular guidewire in the vasculature of the patient in accordance with the modified path (414).

In some embodiments, the system 100 therefore may generate a path for traversing through a vasculature of a patient by a magnetically steerable intravascular guidewire 107 prior to an operation and identify one or more points for review by a user prior to the operation and then, during the operation, the magnetic steering control component 103 may direct at least one of a medical robot arm and a motorized guidewire advancing unit to move the magnetically steerable intravascular guidewire 107 in a manner that will result in the magnetically steerable intravascular guidewire 107 traversing the specified path. By providing technology to generate a path and identify critical points along the path where a user confirmation may improve the accuracy of the generated path prior to onset of an operation, and then communicating during the operation with the medical robot arm and/or motorized guidewire advancing unit, the methods and systems described herein provide improvements to technology for manipulating guidewires through patient vasculature during operations. In some embodiments, by providing technology that generates and displays three-dimensional images of patient vasculature before and during an operation, the methods and systems described herein provide improvements to technology for manipulating guidewires through patient vasculature during operations.

In some embodiments, the system 100 includes non-transitory, computer-readable medium comprising computer program instructions tangibly stored on the non-transitory computer-readable medium, wherein the instructions are executable by at least one processor to perform each of the steps described above in connection with FIGS. 2-4.

It should be understood that the systems described above may provide multiple ones of any or each of those components and these components may be provided on either a standalone machine or, in some embodiments, on multiple machines in a distributed system. The phrases 'in one embodiment,' 'in another embodiment,' and the like, generally mean that the particular feature, structure, step, or characteristic following the phrase is included in at least one embodiment of the present disclosure and may be included in more than one embodiment of the present disclosure. Such phrases may, but do not necessarily, refer to the same embodiment. However, the scope of protection is defined by the appended claims; the embodiments mentioned herein provide examples.

The terms "A or B", "at least one of A or/and B", "at least one of A and B", "at least one of A or B", or "one or more of A or/and B" used in the various embodiments of the present disclosure include any and all combinations of words enumerated with it. For example, "A or B", "at least one of A and B" or "at least one of A or B" may mean (1) including at least one A, (2) including at least one B, (3) including either A or B, or (4) including both at least one A and at least one B.

Any step or act disclosed herein as being performed, or capable of being performed, by a computer or other machine, may be performed automatically by a computer or other machine, whether or not explicitly disclosed as such herein. A step or act that is performed automatically is performed solely by a computer or other machine, without human intervention. A step or act that is performed automatically may, for example, operate solely on inputs received from a computer or other machine, and not from a human. A step or act that is performed automatically may, for example, be initiated by a signal received from a computer or other machine, and not from a human. A step or act that is performed automatically may, for example, provide output to a computer or other machine, and not to a human.

Although terms such as "optimize" and "optimal" may be used herein, in practice, embodiments of the present invention may include methods which produce outputs that are not optimal, or which are not known to be optimal, but which nevertheless are useful. For example, embodiments of the present invention may produce an output which approximates an optimal solution, within some degree of error. As a result, terms herein such as "optimize" and "optimal" should be understood to refer not only to processes which produce optimal outputs, but also processes which produce outputs that approximate an optimal solution, within some degree of error.

The systems and methods described above may be implemented as a method, apparatus, or article of manufacture using programming and/or engineering techniques to produce software, firmware, hardware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices.

Each computer program within the scope of the claims below may be implemented in any programming language, such as assembly language, machine language, a high-level procedural programming language, or an object-oriented programming language. The programming language may, for example, be LISP, PROLOG, PERL, C, C++, C #, JAVA, Python, Rust, Go, or any compiled or interpreted programming language.

Each such computer program may be implemented in a computer program product tangibly embodied in a machine-readable storage device for execution by a computer processor. Method steps may be performed by a computer processor executing a program tangibly embodied on a computer-readable medium to perform functions of the methods and systems described herein by operating on input and generating output. Suitable processors include, by way of example, both general and special purpose microprocessors. Generally, the processor receives instructions and data from a read-only memory and/or a random access memory. Storage devices suitable for tangibly embodying computer program instructions include, for example, all forms of computer-readable devices, firmware, programmable logic, hardware (e.g., integrated circuit chip; electronic devices; a computer-readable non-volatile storage unit; non-volatile memory, such as semiconductor memory devices, including EPROM, EEPROM, and flash memory devices; magnetic disks such as internal hard disks and removable disks; magneto-optical disks; and CD-ROMs). Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium. A computer may also receive programs and data (including, for example, instructions for storage on non-transitory computer-readable media) from a second computer providing access to the programs via a network transmission line, wireless transmission media, signals propagating through space, radio waves, infrared signals, etc.

Figure 5A:
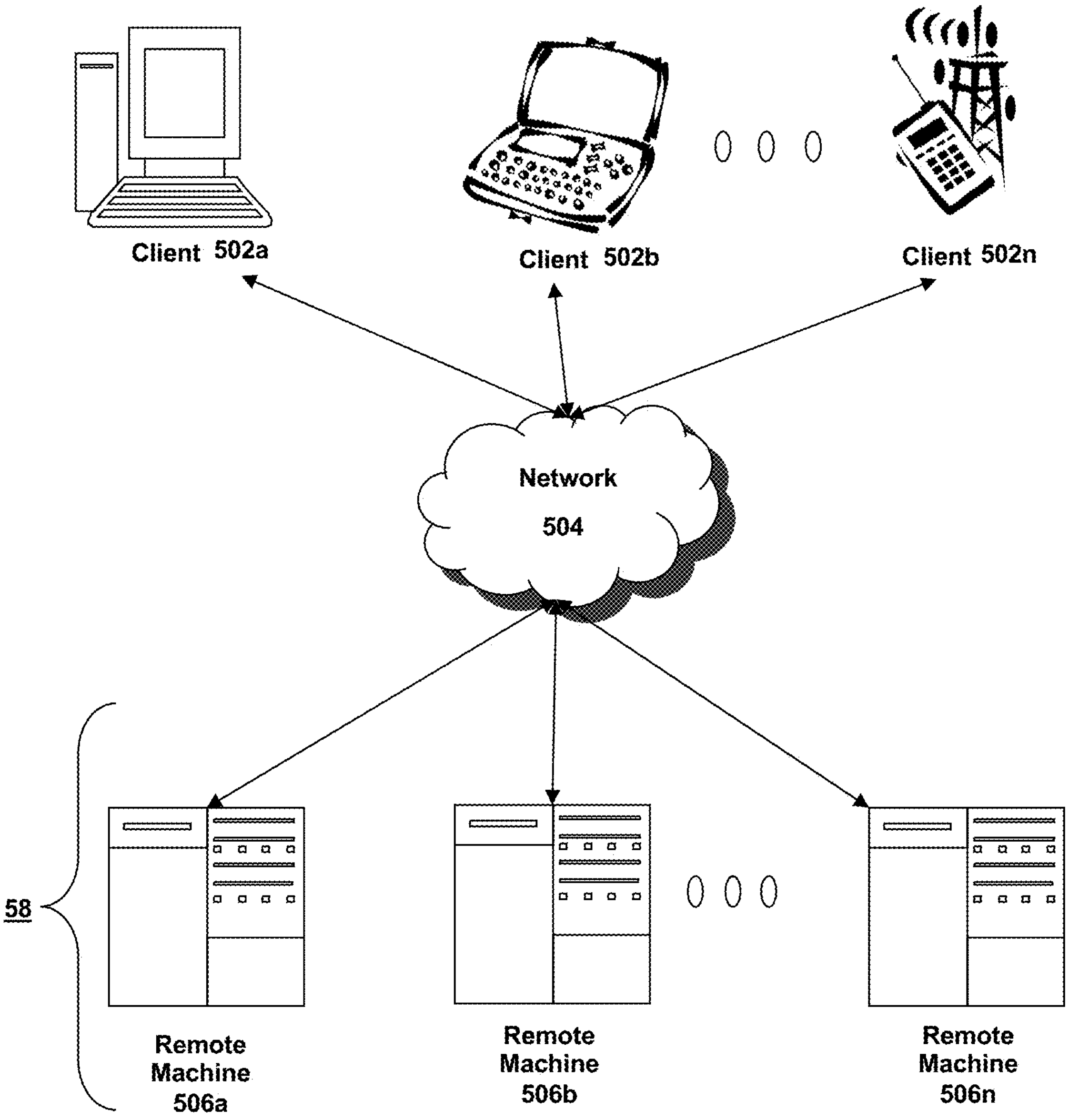
FIGS. 5A-5C are block diagrams depicting embodiments of computers useful in connection with the methods and systems described herein.
Figure 5B:
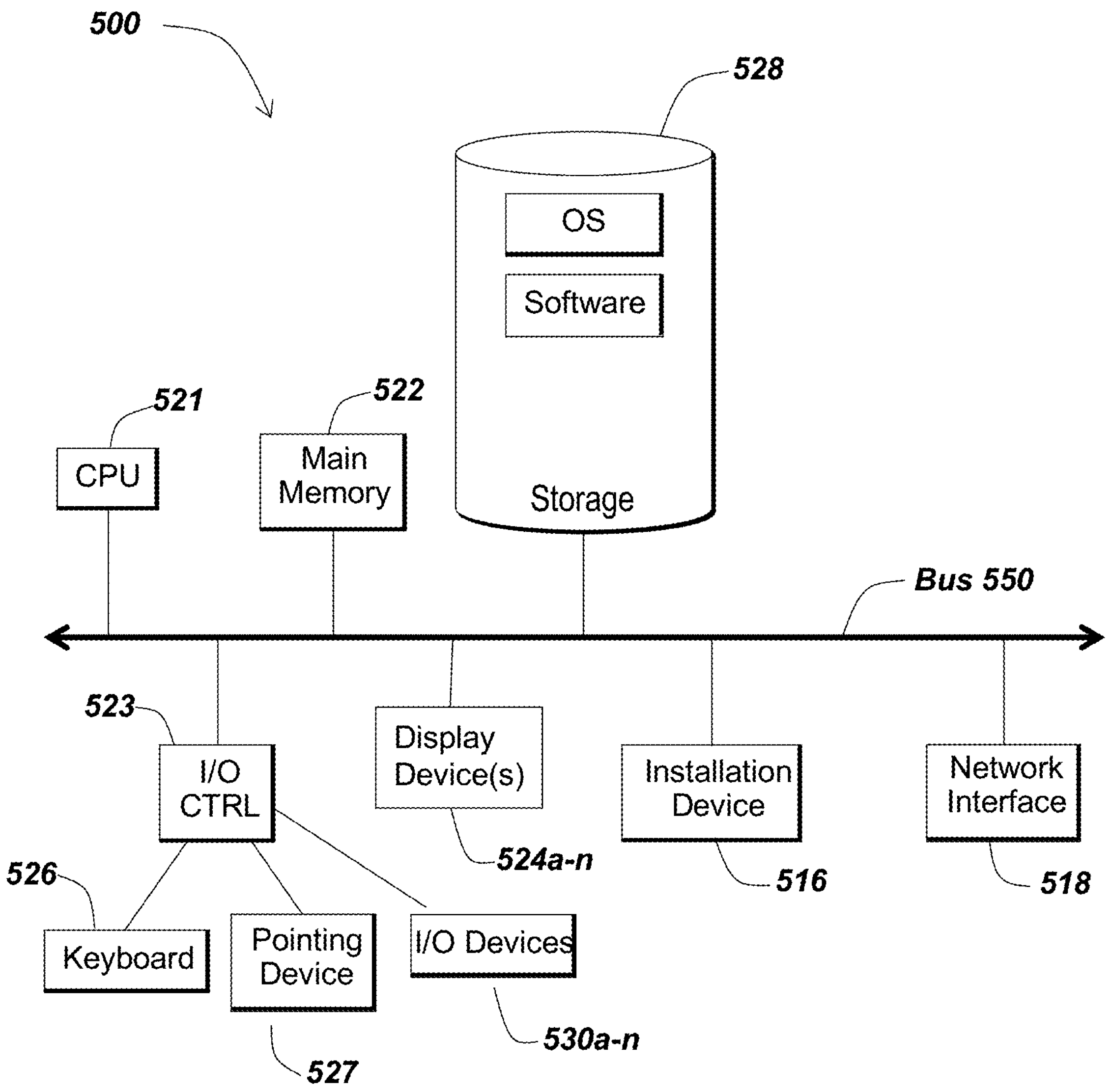
Figure 5C:
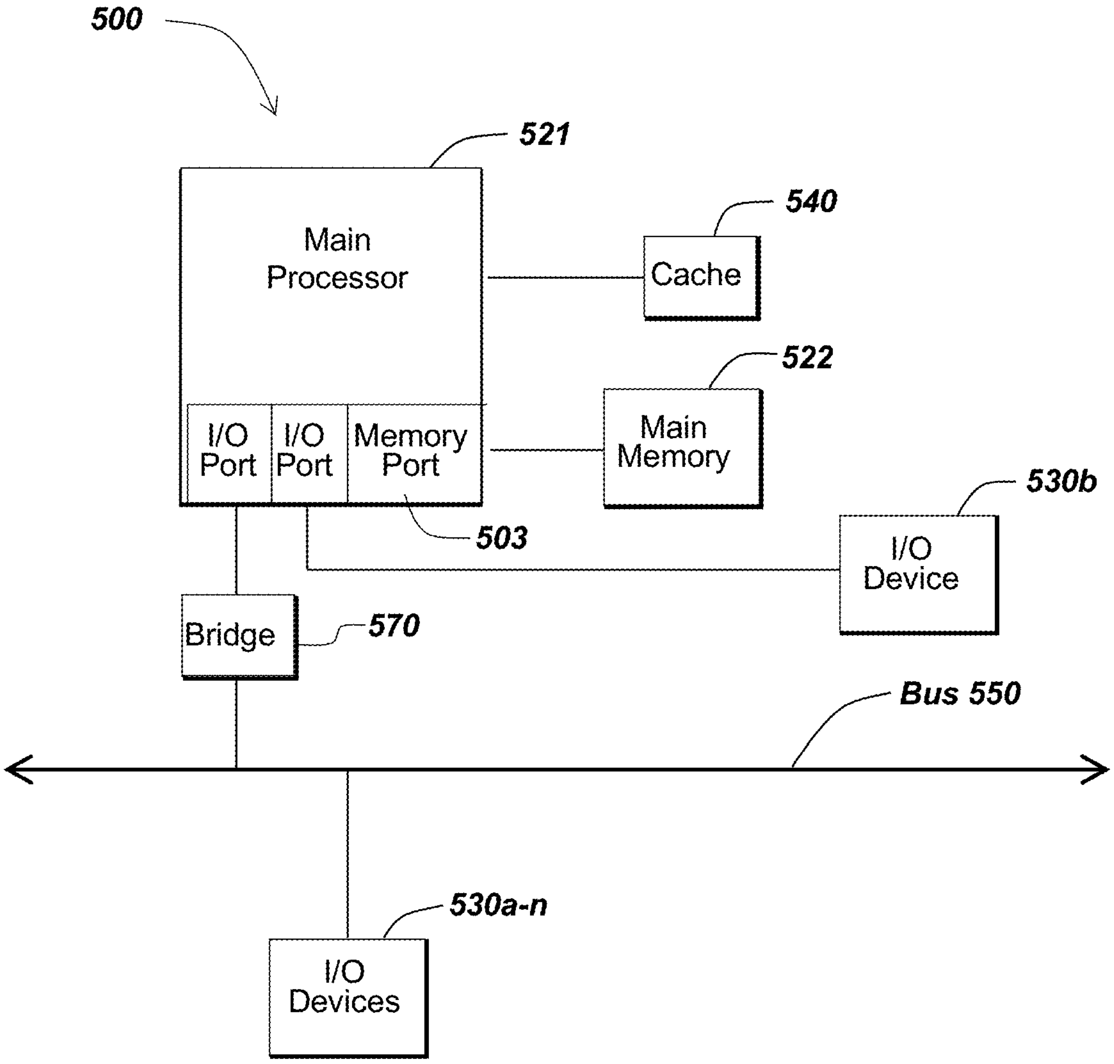

Referring now to FIGS. 5A, 5B, and 5C, block diagrams depict additional detail regarding computing devices that may be modified to execute novel, non-obvious functionality for implementing the methods and systems described above.

Referring now to FIG. 5A, an embodiment of a network environment is depicted. In brief overview, the network environment comprises one or more clients 502*a*-502*n* (also generally referred to as local machine(s) 502, client(s) 502, client node(s) 502, client machine(s) 502, client computer(s) 502, client device(s) 502, computing device(s) 502, endpoint(s) 502, or endpoint node(s) 502) in communication with one or more remote machines 506*a*-506*n* (also generally referred to as server(s) 506 or computing device(s) 506) via one or more networks 504. Any communication disclosed herein, such as communication shown in FIG. 1A, may occur over any embodiment of the network environment depicted in FIG. 5A.

Although FIG. 5A shows a network 504 between the clients 502 and the remote machines 506, the clients 502 and the remote machines 506 may be on the same network 504. The network 504 can be a local area network (LAN), such as a company Intranet, a metropolitan area network (MAN), or a wide area network (WAN), such as the Internet or the World Wide Web. In some embodiments, there are multiple networks 504 between the clients 502 and the remote machines 506. In one of these embodiments, a network 504' (not shown) may be a private network and a network 504 may be a public network. In another of these embodiments, a network 504 may be a private network and a network 504' a public network. In still another embodiment, networks 504 and 504' may both be private networks. In yet another embodiment, networks 504 and 504' may both be public networks.

The network 504 may be any type and/or form of network and may include any of the following: a point to point network, a broadcast network, a wide area network, a local area network, a telecommunications network, a data communication network, a computer network, an ATM (Asynchronous Transfer Mode) network, a SONET (Synchronous Optical Network) network, an SDH (Synchronous Digital Hierarchy) network, a wireless network, a wireline network, an Ethernet, a virtual private network (VPN), a software-defined network (SDN), a network within the cloud such as AWS VPC (Virtual Private Cloud) network or Azure Virtual Network (VNet), and a RDMA (Remote Direct Memory Access) network. In some embodiments, the network 504 may comprise a wireless link, such as an infrared channel or satellite band. The topology of the network 504 may be a bus, star, or ring network topology. The network 504 may be of any such network topology as known to those ordinarily skilled in the art capable of supporting the operations described herein. The network may comprise mobile telephone networks utilizing any protocol or protocols used to communicate among mobile devices (including tables and handheld devices generally), including AMPS, TDMA, CDMA, GSM, GPRS, UMTS, or LTE. In some embodiments, different types of data may be transmitted via different protocols. In other embodiments, the same types of data may be transmitted via different protocols.

A client 502 and a remote machine 506 (referred to generally as computing devices 500 or as machines 500) can be any workstation, desktop computer, laptop or notebook computer, server, portable computer, mobile telephone, mobile smartphone, or other portable telecommunication device, media playing device, a gaming system, mobile computing device, or any other type and/or form of computing, telecommunications or media device that is capable of communicating on any type and form of network and that has sufficient processor power and memory capacity to perform the operations described herein. A client 502 may execute, operate or otherwise provide an application, which can be any type and/or form of software, program, or executable instructions, including, without limitation, any type and/or form of web browser, web-based client, client-server application, an ActiveX control, a JAVA applet, a webserver, a database, an HPC (high performance computing) application, a data processing application, or any other type and/or form of executable instructions capable of executing on client 502.

In one embodiment, a computing device 506 provides functionality of a web server. The web server may be any type of web server, including web servers that are open-source web servers, web servers that execute proprietary software, and cloud-based web servers where a third party hosts the hardware executing the functionality of the web server. In some embodiments, a web server 506 comprises an open-source web server, such as the APACHE servers maintained by the Apache Software Foundation of Delaware. In other embodiments, the web server executes proprietary software, such as the INTERNET INFORMATION SERVICES products provided by Microsoft Corporation of Redmond, WA, the ORACLE IPLANET web server products provided by Oracle Corporation of Redwood Shores, CA, or the ORACLE WEBLOGIC products provided by Oracle Corporation of Redwood Shores, CA.

In some embodiments, the system may include multiple, logically-grouped remote machines 506. In one of these embodiments, the logical group of remote machines may be referred to as a server farm 538. In another of these embodiments, the server farm 538 may be administered as a single entity.

FIGS. 5B and 5C depict block diagrams of a computing device 500 useful for practicing an embodiment of the client 502 or a remote machine 506. As shown in FIGS. 5B and 5C, each computing device 500 includes a central processing unit 521, and a main memory unit 522. As shown in FIG. 5B, a computing device 500 may include a storage device 528, an installation device 516, a network interface 518, an I/O controller 523, display devices 524*a-n*, a keyboard 526, a pointing device 527, such as a mouse, and one or more other I/O devices 530*a-n*. The storage device 528 may include, without limitation, an operating system and software. As shown in FIG. 5C, each computing device 500 may also include additional optional elements, such as a memory port 503, a bridge 570, one or more input/output devices 530*a-n* (generally referred to using reference numeral 530), and a cache memory 540 in communication with the central processing unit 521.

The central processing unit 521 is any logic circuitry that responds to and processes instructions fetched from the main memory unit 522. In many embodiments, the central processing unit 521 is provided by a microprocessor unit, such as: those manufactured by Intel Corporation of Mountain View, CA; those manufactured by Motorola Corporation of Schaumburg, IL; those manufactured by Transmeta Corporation of Santa Clara, CA; those manufactured by International Business Machines of White Plains, NY; or those manufactured by Advanced Micro Devices of Sunnyvale, CA. Other examples include RISC-V processors, SPARC processors, ARM processors, processors used to build UNIX/LINUX "white" boxes, and processors for mobile devices. The computing device 500 may be based on any of these processors, or any other processor capable of operating as described herein.

Main memory unit 522 may be one or more memory chips capable of storing data and allowing any storage location to be directly accessed by the microprocessor 521. The main memory unit 522 may be based on any available memory chips capable of operating as described herein. In the embodiment shown in FIG. 5B, the processor 521 communicates with main memory unit 522 via a system bus 550. FIG. 5C depicts an embodiment of a computing device 500 in which the processor communicates directly with main memory unit 522 via a memory port 503. FIG. 5C also depicts an embodiment in which the main processor 521 communicates directly with cache memory 540 via a secondary bus, sometimes referred to as a backside bus. In other embodiments, the main processor 521 communicates with cache memory 540 using the system bus 550.

In the embodiment shown in FIG. 5B, the processor 521 communicates with various I/O devices 530 via a local system bus 550. Various buses may be used to connect the central processing unit 521 to any of the I/O devices 530, including a VESA VL bus, an ISA bus, an EISA bus, a MicroChannel Architecture (MCA) bus, a PCI bus, a PCI-X bus, a PCI-Express bus, or a NuBus. For embodiments in which the I/O device is a video display device 524, the processor 521 may use an Advanced Graphics Port (AGP) to communicate with the video display device 524. FIG. 5C depicts an embodiment of a computing device 500 in which the main processor 521 also communicates directly with an I/O device 530*b* via, for example, HYPERTRANSPORT, RAPIDIO, or INFINIBAND communications technology.

One or more of a wide variety of I/O devices 530*a-n* may be present in or connected to the computing device 500, each of which may be of the same or different type and/or form. Input devices include keyboards, mice, trackpads, trackballs, microphones, scanners, cameras, and drawing tablets. Output devices include video displays, speakers, inkjet printers, laser printers, 5D printers, and dye-sublimation printers. The I/O devices may be controlled by an I/O controller 523 as shown in FIG. 5B. Furthermore, an I/O device may also provide storage and/or an installation medium 516 for the computing device 500. In some embodiments, the computing device 500 may provide USB connections (not shown) to receive handheld USB storage devices such as the USB Flash Drive line of devices manufactured by Twintech Industry, Inc. of Los Alamitos, CA.

Referring still to FIG. 5B, the computing device 500 may support any suitable installation device 516, such as hardware for receiving and interacting with removable storage; e.g., disk drives of any type, CD drives of any type, DVD drives, tape drives of various formats, USB devices, external hard drives, or any other device suitable for installing software and programs. In some embodiments, the computing device 500 may provide functionality for installing software over a network 504. The computing device 500 may further comprise a storage device, such as one or more hard disk drives or redundant arrays of independent disks, for storing an operating system and other software. Alternatively, the computing device 500 may rely on memory chips for storage instead of hard disks.

Furthermore, the computing device 500 may include a network interface 518 to interface to the network 504 through a variety of connections including, but not limited to, standard telephone lines, LAN or WAN links (e.g., 802.11, T1, T3, 56 kb, X.25, SNA, DECNET, RDMA), broadband connections (e.g., ISDN, Frame Relay, ATM, Gigabit Ethernet, Ethernet-over-SONET), wireless connections, virtual private network (VPN) connections, or some combination of any or all of the above. Connections can be established using a variety of communication protocols (e.g., TCP/IP, IPX, SPX, NetBIOS, Ethernet, ARCNET, SONET, SDH, Fiber Distributed Data Interface (FDDI), RS232, IEEE 802.11, IEEE 802.11a, IEEE 802.11b, IEEE 802.11g, IEEE 802.11n, 802.15.4, Bluetooth, ZIGBEE, CDMA, GSM, WiMax, and direct asynchronous connections). In one embodiment, the computing device 500 communicates with other computing devices 500' via any type and/or form of gateway or tunneling protocol such as GRE, VXLAN, IPIP, SIT, ip6tnl, VTI and VTI6, IP6GRE, FOU, GUE, GENEVE, ERSPAN, Secure Socket Layer (SSL) or Transport Layer Security (TLS). The network interface 518 may comprise a built-in network adapter, network interface card, PCMCIA network card, card bus network adapter, wireless network adapter, USB network adapter, modem, or any other device suitable for interfacing the computing device 500 to any type of network capable of communication and performing the operations described herein.

In further embodiments, an I/O device 530 may be a bridge 570 between the system bus 550 and an external communication bus, such as a USB bus, an Apple Desktop Bus, an RS-232 serial connection, a SCSI bus, a FireWire bus, a FireWire 800 bus, an Ethernet bus, an AppleTalk bus, a Gigabit Ethernet bus, an Asynchronous Transfer Mode bus, a HIPPI bus, a Super HIPPI bus, a Serial Plus bus, a SCI/LAMP bus, a Fibre Channel bus, or a Serial Attached small computer system interface bus.

A computing device 500 of the sort depicted in FIGS. 5B and 5C typically operates under the control of operating systems, which control scheduling of tasks and access to system resources. The computing device 500 can be running any operating system such as any of the versions of the MICROSOFT WINDOWS operating systems, the different releases of the UNIX and LINUX operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 7, WINDOWS 8, WINDOWS VISTA, WINDOWS 10, and WINDOWS 11 all of which are manufactured by Microsoft Corporation of Redmond, WA; MAC OS manufactured by Apple Inc. of Cupertino, CA; OS/2 manufactured by International Business Machines of Armonk, NY; Red Hat Enterprise Linux, a Linux-variant operating system distributed by Red Hat, Inc., of Raleigh, NC; Ubuntu, a freely-available operating system distributed by Canonical Ltd. of London, England; CentOS, a freely-available operating system distributed by the centos.org community; SUSE Linux, a freely-available operating system distributed by SUSE, or any type and/or form of a Unix operating system, among others.

Having described certain embodiments of methods and systems for automated steering of guidewire, it will be apparent to one of skill in the art that other embodiments incorporating the concepts of the disclosure may be used. Therefore, the disclosure should not be limited to certain embodiments, but rather should be limited only by the spirit and scope of the following claims.

What is claimed is:

1. A method for automated generation of three-dimensional vessel maps and automated steering of guidewires through vasculature represented by the generated three-dimensional vessel maps, the method comprising:

accessing, by a magnetic steering control component, volumetric imaging associated with a patient;

generating, prior to an operation on the patient, by the magnetic steering control component, a three-dimensional vessel map based upon the accessed volumetric imaging;

generating, prior to the operation, by the magnetic steering control component, a path from an initial point in a vasculature of the patient to a target location in the vasculature based upon the generated three-dimensional vessel map;

displaying, prior to the operation, by the magnetic steering control component, in a graphical user interface, the three-dimensional vessel map and the generated path;

receiving, prior to the operation, by the magnetic steering control component, from the graphical user interface, input representing a modification to the generated path;

modifying, prior to the operation, by the magnetic steering control component, the generated path based upon the received input; and directing, during the operation, by the magnetic steering control component, at least one of a medical robot arm and a motorized guidewire advancing unit to modify a location of a magnetically steerable intravascular guidewire through the vasculature of the patient in accordance with the modified path.

2. The method of claim 1, wherein generating the path from the initial point in the vasculature of the patient to the target location in the vasculature further comprises:

accessing data associated with a type of the operation; and using the accessed data associated with a type of the operation in generating the path.

3. The method of claim 1, wherein displaying the graphical user interface further comprises modifying the graphical user interface to include a display of a graphical user interface element identifying a node in a plurality of nodes, wherein each node represents a location on the generated path at which there is a branch in the vessel map and through which the magnetically steerable intravascular guidewire will navigate during the operation.

4. The method of claim 3, wherein displaying the graphical user interface to include the display of the graphical user interface element identifying the node further comprises modifying a visual characteristic of the graphical user interface element identifying the node to indicate that the node is an upcoming node in the plurality of nodes on the generated path.

5. The method of claim 3, wherein displaying the graphical user interface further comprises modifying the graphical user interface during the operation.

6. The method of claim 5, wherein displaying the graphical user interface during operation further comprises modifying the graphical user interface to include a display of a second graphical user interface element identifying a second node that is at an upcoming location along the path at which the vessel branches and where the magnetically steerable intravascular guidewire will navigate the branch.

7. The method of claim 6, wherein displaying the graphical user interface during operation further comprises modifying the graphical user interface to remove the display of the second graphical user interface element subsequent to navigation to the second node by the magnetically steerable intravascular guidewire.

8. The method of claim 1, wherein receiving the input representing the modification further comprises receiving user input identifying a direction for the magnetically steerable intravascular guidewire to take at a branch in the vasculature.

9. The method of claim 1, wherein receiving the input representing the modification further comprises receiving user input modifying an orientation of a magnetic field of a magnet in the magnetically steerable intravascular guidewire.

10. The method of claim 1, wherein receiving the input representing the modification further comprises receiving user input identifying a direction that is different from a direction included in the generated path for the magnetically steerable intravascular guidewire to take at a branch in the vasculature.

11. The method of claim 1, wherein receiving the input representing the modification further comprises receiving user input confirming a direction included in the generated path for the magnetically steerable intravascular guidewire to take at a branch in the vasculature.

12. The method of claim 1, wherein directing the modification of the location of the magnetically steerable intravascular guidewire through the vasculature of the patient in accordance with the modified path further comprises transmitting at least one direction to the medical robot arm in a format processable by the medical robot arm.

13. The method of claim 1, wherein directing the modification of the location of the magnetically steerable intravascular guidewire through the vasculature of the patient in accordance with the modified path further comprises displaying at least one direction in the graphical user interface.

14. The method of claim 13, wherein directing the modification of the location of the magnetically steerable intravascular guidewire through the vasculature of the patient in accordance with the modified path further comprises directing a user to interact with a physical interface component to modify the location of the magnetically steerable intravascular guidewire.

15. The method of claim 1 further comprising displaying, during the operation, the graphical user interface displaying the three-dimensional vessel map and the generated path.

16. The method of claim 1 further comprising receiving, during the operation, from the graphical user interface, input representing a modification to the generated path.

17. The method of claim 16 further comprising modifying, during the operation, the generated path based upon the received input.

18. The method of claim 1, wherein directing the medical robot arm further comprises executing, by the magnetic steering control component, at least one motion-planning and optimization algorithm, to automatically calculate (i) a position and orientation of an actuating magnet in proximity to the patient to generate a magnetic field that is aligned with a user-specified steering direction and (ii) a joint configuration of the medical robot arm that corresponds to the calculated position and orientation of the actuating magnet.

19. The method of claim 18, wherein executing the at least one motion-planning and optimization algorithm further comprises automatically calculating a position and orientation of the actuating magnet that avoids collision with an object in proximity to the medical robot arm.

20. The method of claim 18, wherein executing the at least one motion-planning and optimization algorithm further comprises automatically calculating the joint configuration of the medical robot arm that corresponds to the calculated position and orientation of the actuating magnet and that avoids collision with an object in proximity to the medical robot arm.

21. The method of claim 18, wherein executing the at least one motion-planning and optimization algorithm further comprises automatically calculating a kinematic trajectory of the medical robot arm that avoids a collision with an object in proximity to the medical robot arm.

* * * * *